United States Patent [19]

Roby et al.

[11] Patent Number: 5,536,875

[45] Date of Patent: Jul. 16, 1996

[54] ENHANCED OXIDATION OF ORGANIC CHEMICALS

[75] Inventors: Anne K. Roby, Peekskill; Jeffrey P. Kingsley, Newburgh, both of N.Y.

[73] Assignee: Praxair Technology, Inc., Danbury, Conn.

[21] Appl. No.: 447,327

[22] Filed: May 22, 1995

Related U.S. Application Data

[62] Division of Ser. No. 241,444, May 11, 1994.

[51] Int. Cl.$^6$ .................................................. C07C 51/16
[52] U.S. Cl. ............................................ 562/412; 562/407
[58] Field of Search ...................................... 562/407, 412

[56] References Cited

U.S. PATENT DOCUMENTS 4,900,480  2/1990  Litz et al. .............................. 261/36.1

Primary Examiner—José G. Dees
Assistant Examiner—Samuel Barts
Attorney, Agent, or Firm—Alvin H. Fritschler

[57] ABSTRACT

Organic chemical oxidation reactions are carried out using pure or nearly pure oxygen and evaporative cooling. Advantageous operating results are achieved thereby, and the oxidation of organic chemicals resulting in the production of solid products or byproducts is facilitated by obviating the need for direct contact heat exchange surfaces that become coated with solid products or byproducts.

10 Claims, 2 Drawing Sheets

ENHANCED OXIDATION OF ORGANIC CHEMICALS

This application is a Division of prior U.S. application Ser. No. 08/241,444 Filing Date May 11, 1994.

BACKGROUND OF THE INVENTION

1. Field of the Invention

The invention relates to the mixing of gases and liquids. More particularly, it relates to the oxidation of organic chemicals with pure or nearly pure oxygen.

2. Description of the Prior Art

In organic chemical oxidation reactions in which the oxidation products or byproducts are not precipitated in the reactor as solid materials, direct contact cooling, as by the use of cooling coils, is conveniently used to remove the heat of reaction. In three phase systems in which some portion of the reaction mixture is a precipitating solid phase, however, the precipitation of solids on the heat transfer surfaces can rapidly reduce the transfer capacity of said surfaces. In addition, the surface area of the heat transfer surfaces for the removal of heat in highly exothermic organic chemical oxidation reactions can be quite large relative to the reactor volume.

Most commercial liquid phase oxidations of organic chemicals are carried out using air as a convenient source of oxygen. In such oxidation processes, the inert nitrogen component of the feed air strips off a portion of the volatile components in the reaction mixture. The cooling effect due to the latent heat removal through such evaporation thus balances the exothermic heat of the oxidation reaction. For a given amount of excess air, or inert gas flow through the oxidation reactor, a relationship exists between the temperature of the oxidation reactor and the operating pressure at which the oxidation reaction is carried out. This relationship between the reaction temperature and pressure depends on the composition of the reaction mixture and the volume of excess gas employed. Air based evaporative cooling processes generally require relatively high pressure and temperature conditions for any given organic chemical oxidation.

The feed air passing to the reactor must be compressed to a pressure somewhat above the reactor operating pressure before it is blown into the reactor through a pipe or other submerged sparger. As the air bubbles are dispersed and circulated throughout the liquid phase, the oxygen concentration in said bubbles decreases as the oxygen dissolves and reacts with the organic chemical in the liquid phase. The air bubbles disengage from the liquid phase and collect at the top of the reactor to form a continuous gas phase. This overhead gas phase constitutes a waste gas that must be vented in order to provide room fresh feed air while maintaining adequate gas hold-up to promote the desired transfer of oxygen from the feed air to the organic chemical-containing liquid phase.

To avoid the possibility of fire or explosion, the oxygen concentration in the overhead gas space at the top of the reactor must be maintained below the flammable limit. For this purpose, the oxygen concentration must be maintained at less than 8–9% by volume. More typically, the oxygen concentration in the gas space is maintained below 5% by volume to provide a safe margin below the flammable limit. Thus, in a well stirred tank reactor, the average concentration of undissolved oxygen in the circulating air bubbles must be below 5% in order to insure that the average concentration of oxygen in the gas that collects in the headspace of the reactor is nonflammable.

The oxygen concentration in the gas space is a function of the rate at which feed air is fed to the reactor and the rate of consumption of oxygen from the feed air by reaction with the organic chemical being oxidized. For most liquid phase oxidation reactions, the overall rate of oxygen consumption is determined by the rate at which the oxygen in the gas phase, i.e. gas bubbles, can transfer into the liquid phase. Since the oxygen transfer rate is proportional to the oxygen partial pressure in the gas phase, which is proportional to the volumetric fraction of the oxygen in the gas phase, the 5% oxygen restriction in the gas phase, as referred to above, effectively limits the oxygen mass transfer rate, and therefore, the overall organic chemical oxidation rate.

As air bubbles circulate within the reactor, solvent, water, volatile organic chemicals (VOC's) and byproduct gases, such as $CO_2$ and CO, collect in the continuous overhead gas space, and are vented from the reactor. The total amount of volatile species that leave the reactor with the inert vent gas is proportional to the total gas throughput, which is proportional to the air feed rate.

In the United States of America, applicable federal, state and local air quality standards that pertain to a particular production facility determine the degree to which these volatile species must be removed from the vent gas before being released to the atmosphere. Solvent materials are typically valuable constituents of the oxidation processes, so they are usually condensed and recycled to the reactor. Residual organic compounds are usually stripped from the inert vent gas, thereby producing a liquid waste stream from the stripper bottoms. Some vent gas treatment systems may also include COx abatement systems as needed to meet air quality standards. Since the total amount of material that must be removed from the vent gas is proportional to the air feed rate to the reactor, the size of the vent gas treatment equipment and the amount of waste that is generated in the oxidation process, is similarly proportional to the air feed rate.

Pure or nearly pure oxygen offers many potential advantages in such organic chemical oxidation reactions. However, the safe, efficient addition of pure oxygen feed into oxidation systems requires the use of special precautions because of the potential for fires or explosions. The Litz et al. patent, U.S. Pat. No. 4,800,480, discloses a highly desirable Liquid Oxidation Reactor (LOR) system for use in place of a conventional reactor system, which is not suitable or is inefficient when used with feed oxygen instead of feed air. The LOR system enables gas bubbles to be recirculated with a recirculating flow of a portion of the organic chemical liquid composition, separated from the overhead gas space, in order to enhance the oxygen use efficiency, while avoiding the loss of appreciable amounts of gas to the overhead gas space. As the gas bubbles are recirculated, and as the oxygen is transferred to the liquid phase, the concentration of oxygen in the gas bubbles decreases. The mass transfer advantage offered by the use of pure oxygen is, therefore, diminished.

For organic chemical oxidations that react very rapidly, the oxygen use efficiency is naturally very high. Thus, a high percentage of the oxygen is consumed on the first pass through the impeller means used in the LOR system, and the mass transfer advantage is greatly diminished in subsequent passes through the impeller means. For such systems, the recirculation of the gas bubbles is undesirable. In addition, because of the nature of the downward pumping impeller and surrounding draft tube used in the LOR system as described by Litz, et al., high volumes of gas in the draft tube can cause the mixer device to cavitate. If such cavitation occurs, the impeller can no longer pump liquid or break up and disperse oxygen in the form of fine bubbles in the recirculating body of organic chemical liquid. If it were desired to employ evaporative cooling in place of commonly used direct contact cooling means, the presence of more volatile or vapor in the reactor would be required than for direct contact cooling processes. If large amounts of vapor were to be recirculated into the draft tube, however, undesired cavitation would likely occur and disrupt the desired mixing of the pure oxygen feed and the liquid being oxidized. As evaporative cooling is advantageous in that it eliminates the problems encountered in the use of direct contact heat exchange surfaces, a modification of the LOR impeller/draft tube system is needed in order to reduce the amount of recirculated gas in the reactor, so as to enhance the overall performance of LOR systems as used in evaporatively cooled oxidation processes.

It is an object of the present invention, therefore, to provide a process and system for the oxidation of organic chemicals, using evaporative cooling of the reaction mixture to eliminate the problems associated with the use of direct contact heat exchange surfaces.

It is another object of the invention to provide an LOR process and system using evaporative cooling and pure or nearly pure oxygen for the oxidation of organic liquids.

With these and other objects in mind, the invention is hereinafter described in detail, the novel features thereof being particularly pointed out in the appended claims.

SUMMARY OF THE INVENTION

The LOR system is modified so as to minimize the recirculation of gas bubbles through the draft tube thereof, thereby precluding undesired cavitation therein. Evaporative cooling, which requires a larger amount of vapor in the reactor than is present in direct contact cooling techniques, can thus be advantageously employed in organic chemical oxidation reactions using pure or nearly pure oxygen in which portions of the oxidation products or byproducts are in the solid phase.

BRIEF DESCRIPTION OF THE DRAWINGS

The invention is hereinafter described with reference to the accompanying drawings in which.

DETAILED DESCRIPTION OF THE INVENTION

Figure 1:
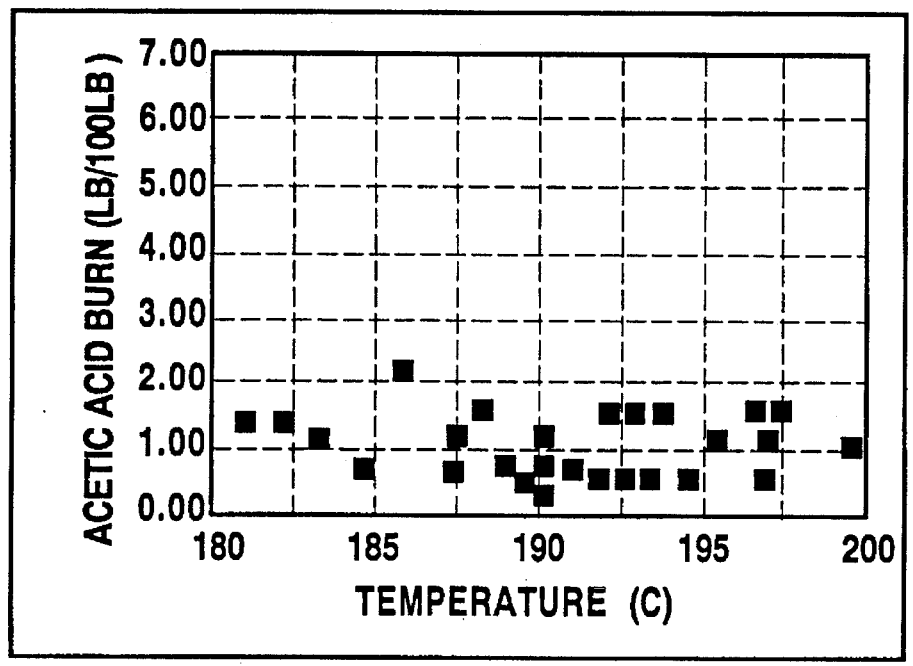
FIG. 1 is a plot of acetic acid burn as a function of temperature in the evaporatively cooled LOR process of the invention.

The objects of the invention are accomplished by carrying out the desired organic chemical oxidation reactions with pure or nearly pure oxygen in a manner enabling evaporative cooling to be employed, particularly with respect to the advantageous use of the LOR process and system for such oxidation purposes. For reactions in which a portion of the oxidation products or byproducts are in the solid phase, the invention avoids the practical operating problems associated with the use of heat exchange surfaces as a result of solids precipitation on the heat transfer surfaces of cooling coils and the like. As a result, the safe and efficient use of pure or nearly pure oxygen for the oxidation of an organic chemical can conveniently be carried out using evaporative cooling to desirably remove the heat of reaction generated during the oxidation reaction. The practice of the invention enables operation of the subject process and system at the boiling point of the oxidation reaction mixture under essentially no excess oxygen conditions.

The use of the modified LOR process and system, as herein described and claimed, for the oxidation of organic chemicals substantially enhances the mass transfer of oxygen from the gas phase to the liquid phase, thus increasing the overall rate of reaction compared to the use of feed air as a source of oxygen. The LOR system as employed for purposes of the invention minimizes the recirculation of gas bubbles through the draft tube, which is desirable since oxygen is largely consumed in the first pass through the downwardly pumping helical impeller/draft tube combination positioned within the reactor and within the roll cells referred to below. For the process of the invention to be economical, the rate at which oxygen is consumed, i.e. transfers to the liquid and reacts with the organic chemical being oxidized, must be very high.

One of the important advantages of the LOR approach of the invention is, that, since the gas-liquid reaction mixture is pumped from the draft tube at high velocities, thereby forming a jet that entrains surrounding liquid outside the draft tube, and impacts on the bottom of the reaction vessel, roll cells are formed in the bottom of the reactor. These roll cells essentially trap the dispersed gas phase until it is either completely consumed or coalesces to a critical bubble diameter having sufficient buoyancy to rise through the liquid and escape. This pattern of fluid dynamics yields very high oxygen use efficiency.

The process conditions for the oxidation of organic compounds in the modified LOR system of the invention will generally be within the range of those practiced commercially in air based oxidation processes. The most significant difference is that, for a given reaction mixture and operating temperature, the operating pressure of the reactor will be lower with the oxygen based process than with the air based process.

It will be noted that for some specific oxidation processes, however, the optimal process conditions, such as operating temperature and catalyst concentration, may be different for the oxygen based reaction than for the corresponding air based reaction. For a typical oxidation reaction, the air based process economics are determined by the relative benefits of high temperature on reaction rate and conversion compared with the increased loss of product selectivity and yield with increased operating temperature conditions. Such loss of selectivity is seen in the increased loss of solvent and/or reactant to waste byproducts, such as carbon dioxide or carbon monoxide. Catalyst concentration can have a similar effect on reaction rate as well as selectivity. With the evaporatively cooled oxygen based process as practiced in accordance with the invention, product conversion and reaction rate are found to increase with increasing operating temperature, but no dependance of solvent loss on reaction temperature has been observed.

With reference to FIG. 1 of the drawing, the solvent acid burn behavior, illustrated as a function of temperature, relates to the oxidation of p-xylene to terephthalic acid in the evaporatively cooled process of the invention. Those skilled in the art will appreciate that the reaction of acetic acid solvent is undesired, and is found to be consistently low relative to the air based processes at typical reaction temperatures ranging from about 180° C. to 200° C. The indicated data was taken in a 3.3L LOR reactor modified in accordance with the invention. The inside diameter of the reactor was 5 inches, and both a 2 inch impeller and a 3 inch impeller were positioned inside a draft tube and were used at a rotational speed of 1,000 rpm, said draft tube being positioned in the reactor as described and claimed herein. The feed mix was typically 11% p-xylene. The reaction catalysts employed were cobalt and manganese, as acetate salts, ranging in concentrations of from 200 to 2,000 ppm, and from 500 to 3,000 ppm, respectively. Bromine, in the form of hydrogen bromide, was used as an initiator with concentrations in the feed mix ranging from 400 to 3,000 rpm.

Figure 2:
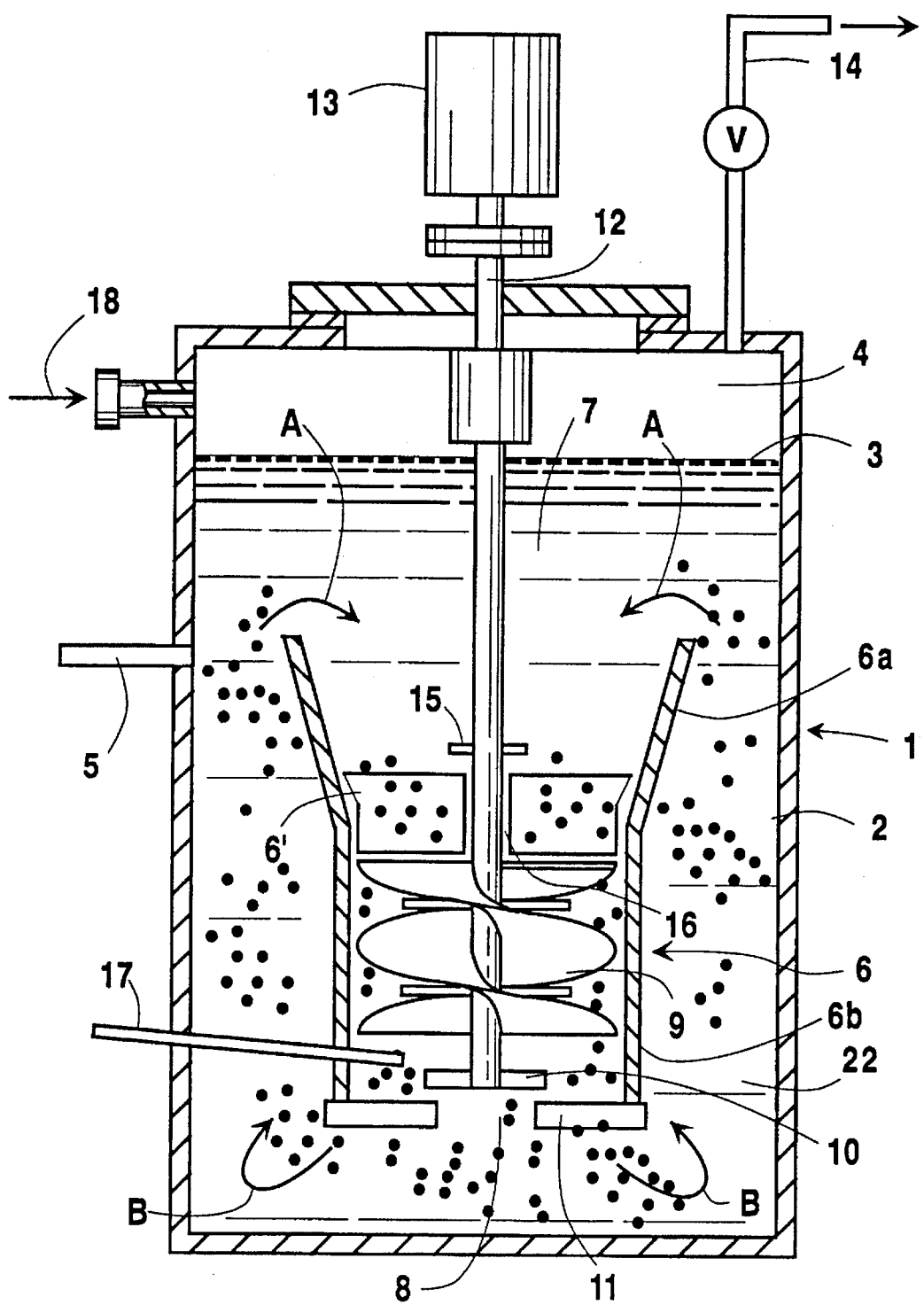
FIG. 2 is a schematic side elevational view of an LOR mixing vessel representing an embodiment of the invention.

FIG. 2 of the drawings illustrates a modified LOR system suitable for use in accordance with the invention for the oxidation of organic liquids with pure or nearly pure oxygen, using evaporative cooling of the reaction mixture. In this embodiment, reactor vessel 1 has a body of organic liquid 2 therein, with gas-liquid interface 3 and overhead gas phase 4. Product liquid is removed from reactor vessel 1 through line 5. As in LOR system of Litz et al., hollow draft tube 6 is typically centrally positioned within reactor vessel 1, with open end 7 at the top and open end 8 at the bottom thereof. Impeller means 9 are positioned within hollow draft tube 6. Such impeller means 9 are downward pumping helical impeller means adapted to facilitate the downward flow of liquid at high velocity from said body of liquid 2 in hollow draft tube 6, the formation of turbulent roll cells B, and the upward flow of said liquid therefrom in the annulus between the side roll of reactor vessel and the outside of hollow draft tube 6 above said roll cells B. Impeller means 9 commonly include radial flow impeller means 10 and, if desired, lower baffle means 11 to facilitate the desired recirculating flow of liquid in reactor vessel 1. A suitable drive shaft 12 that extends upward from reactor vessel 1 for connection to suitable driving means 13 used to operate impeller means 9.

In FIG. 2 of the Litz et al. patent, it will be noted that hollow draft chamber 29 optimally includes a conically flared portion 30a at the upper end thereof for purposes of facilitating the flow of a gas bubbleliquid mixture into the draft chamber for downward passage therein. In the modified LOR system of the invention, a conically flared portion is likewise positioned at the upper end of the hollow draft tube 6, but the configuration of said conically flared portion is quite different than that of Litz et al., and it is used for the opposite purpose of reducing the amount of gas bubbles drawn downward into hollow draft tube 6. Thus, vertically elongated, conically flared portion 6a of hollow draft tube 6 extends upward above the generally cylindrical bottom portion 6b thereof in which impeller means 9 is positioned. The increase in diameter at the top of said conically flared portion 6a serves to minimize the downward velocity of liquid flow pattern A across the top of said hollow draft tube 6, thereby appreciably reducing the portion of the gas bubbles rising in the reactor vessel outside said hollow draft tube 6 that are drawn down into impeller means 9 with the downward flow of reactant liquid in hollow draft tube 6. For this purpose, vertically elongated, conically flared upper portion 6a extends in vertical distance from about 0% to about 200%, preferably about 100% to about 150%, of the length of the bottom portion b of said hollow draft tube, in which impeller means 9 are positioned, and which is typically of cylindrical, nontapered configuration. The diameter at the top of said draft tube, i.e., the enlarged diameter at the top of upper portion 6a, is appropriately sized to minimize the downward velocity of liquid across the top of the draft tube, e.g., to about 1.5 ft./sec. in certain embodiments. While the dimensions of said upper portion 6a of draft tube 6 will be understood to vary depending on the overall circumstances of a given application, a clearance of from about 0.5 to about 4.0 times the diameter of the draft tube will typically pertain between said upper portion 6a and the walls of the reaction vessel. In some instances, the enlarged diameter at the top of upper portion 6a will be from 1.5 to 3.0 times the diameter of bottom portion 6b. In particular embodiments the enlarged diameter at the top of upper portion 6a will be from about 40% to about 80% of the inside diamter or width of reactor vessel, preferably about 50% to 60% thereof. The geometry and rotational speed of the impeller means are factors in determining the size of draft tube 6, and upper portion 6a thereof, for a particular application. The high velocity of the liquid pumped downward through the impeller means will typically be in the range of from 5 or 6 to about 8 ft./sec. or more, such as to create the high turbulent roll cells that trap undissolved oxygen and enhance the desired dissolution thereof. Baffle means 6' is also desirably positioned in said conically flared portion 6a of hollow draft tube 6 to facilitate the downward flow of liquid to impeller means 9.

As a result of the rapid consumption of feed oxygen upon injection into hollow draft tube 6, and the minimizing of the downward flow of liquid across the top of said draft tube, the modified LOR impeller/draft tube combination of the invention effectively reduces the amount of recirculated gas passing downward in the draft tube. The gas bubbles passing upward in the reaction vessel outside bottom portion 6b of the hollow draft tube comprise principally volatile organic chemicals (VOCs), reactant solvent, water vapor and by products, such as CO and $CO_2$, with only small amounts of undissolved oxygen being present therein. The evaporation of the volatile organic species provides the evaporative cooling needed to remove the heat of reaction of the desired organic chemical oxidation operation. It will be seen that the gas bubbles rising in reactor vessel 1, particularly in the vicinity of the top of upper portion 6a of hollow draft tube 6, and in the region above the draft tube to gas-liquid interface 3 contain very little oxygen, so that the oxygen concentration in overhead gas phase 4 is readily maintained within the indicated limits to assure against the possibility of fire or explosion. The region of the body of liquid 2 near the top upper portion 6a hollow draft tube 6 and in the portion of liquid body 2 above said upper portion 6a thus constitutes, in effect, a relatively quiescent zone of less turbulence analogous to that provided in the LOR process and system of the Litz et al. patent. It will be understood that gases are vented from overhead gas phase 4, through vent means 14, during the oxidation reaction process. For purposes of the invention, it should also be noted that the lower nonflared portion 6b of hollow draft tube 6 is desirably positioned in the lower half of reaction vessel 1, as shown in FIG. 2, preferably near the bottom of said vessel so as to provide impact between the gas bubble-liquid mixture being discharged from the bottom of reactor vessel 1 and said bottom of the vessel.

In furtherance of the entirely different gas flow patterns desired in the practice of the invention visa-vis the gas-liquid mixing operating described in the Litz et al. patent, baffle means corresponding to guide baffle means 34, used in the Litz et al. system to direct a gas bubble-liquid mixture to the top of hollow draft chamber 29, are not employed in the practice of the invention. The invention does, however, employ a small horizontal baffle means, i.e. disc 15, positioned in hollow draft tube 6 around drive shaft 12 in the region above the impeller means. Such baffle means serve to preclude the ingestion of gas, by vortex action, from overhead gas phase 4 along said drive shaft 12.

As indicated above, the invention, particularly the modified LOR process and system embodiment thereof, uses pure or nearly pure oxygen for the oxidation of organic chemicals, with evaporative cooling being employed to remove the heat of reaction generated by the oxidation reaction. For this purpose, the mass transfer of oxygen from the gas phase to the liquid phase is substantially enhanced so as to increase the overall rate of reaction as compared to air based oxidation reactions. The practice of the invention enables a rapid rate of oxygen consumption to be achieved such that a very high oxygen use efficiency, i.e., at least 75% and preferably 90% or more, is obtained upon first injection of pure or nearly pure oxygen directly into hollow draft tube 6 as herein described. Such pure oxygen utilization, coupled with the configuration of said hollow draft tube 6 as described above, minimizes the recirculation of gas bubbles through said draft tube 6, enables evaporative cooling to be advantageously employed, and precludes undesired cavitation in impeller means 9 that would impede or preclude the desired recirculation of liquid reactant and the breaking up and rapid dispersion of oxygen as bubbles in the liquid reactant.

For purposes of the evaporative cooling approach of the invention, the pure or nearly pure oxygen feed is added to reactor vessel 1 at a point of high turbulence within hollow draft tube 6, or just below it, rather than elsewhere in the body of organic liquid 2. While oxygen addition can be made at any convenient point of high turbulence in said hollow draft tube 6, such as, for example, through injection line 16 directly to lower portion 6b thereof immediately above impeller means 9, it is desirable and convenient to inject oxygen into the system, through injection line 17 to a point in said lower portion 6b below helical impeller means 9 and radial flow impeller means 10, such as flat blade turbines, if employed or to a point in said lower portion 6b between helical impeller means 9 and said radial flow impeller means 10, if employed. It will be appreciated that these are points of high shear. It should be noted that the injection of the oxygen feed at such a point of high turbulence or shear is important to the desired rapid consumption of oxygen. The initially high concentration of oxygen in the gas phase at the point of injection serves to enhance the mass transfer rate of the oxygen into this region of the liquid reactant, which would be otherwise oxygen depleted in the liquid phase due to the rapid rate of the oxidation reaction.

In the practice of the FIG. 2 embodiment of the invention, it will be understood that nitrogen or other inert purge gas can be passed into overhead gas phase 4 through line 18 to maintain a safe oxygen concentration below the flammable limit in said overhead gas phase 4. In this regard, it should be noted that the draft tube configuration is an excellent pump, which sets up the above-indicated roll cells that trap undissolved oxygen, which allows high oxygen efficiency to be achieved and limits the amount of nitrogen or other inert purge gas required in the overhead gas phase compared to the embodiment of FIG. 3 discussed below.

Figure 3:
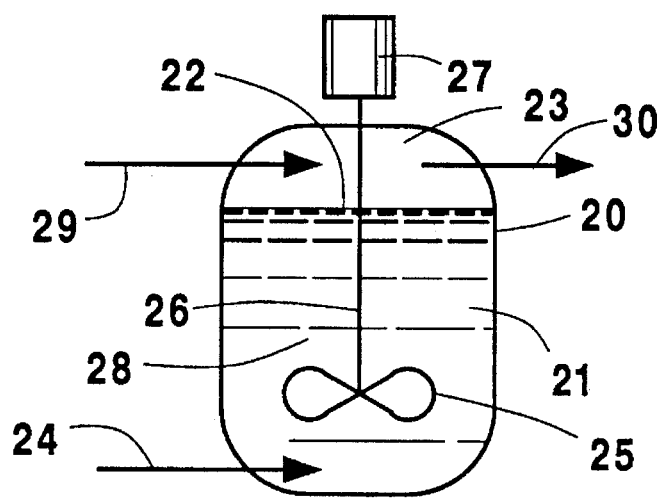
FIG. 3 is a schematic side elevational view of conventional reactor design that can be used in evaporative cooling operations using oxygen in place of air for the oxidation of hydrocarbons.

It should be noted that, in less preferred embodiments, the substitution of oxygen for air in the oxidation of organic chemicals, e.g. hydrocarbons, can be carried out in conventional reactor vessels operating such as to remove the exothermic heat of the oxidation reaction by evaporation cooling. In FIG. 3 of the drawings, reactor vessel 20 containing a body of liquid reactant 21, with gas-liquid interface 22 and overhead gas phase 23, has oxygen injected therein through line 24. Agitation means 25, driven by drive shaft 26 and drive motor 27, is used to disperse the oxygen, desirably injected below said agitation means 25, in the form of bubbles 28 in said body of liquid reactant 21. Nitrogen or other inert vent gas is introduced into overhead gas phase 23 through line 29, and vent gas is withdrawn therefrom through line 30.

By running the oxidation reaction in reactor vessel 20 at the boiling point of the reaction mixture, i.e., with no excess gaseous oxygen, the heat of reaction of the oxidation reaction is removed from the reaction mixture by evaporative cooling. Under such conditions, many of the advantages observed with oxygen based processing, i.e., increased reaction rate, decreased vent flow, reduction in byproduct formation, are realized. However, to avoid safety problems associated with dangerous concentrations of oxygen in overhead gas phase 23 in such reactor operations, a large amount of nitrogen or other inert vent gas must be passed to said overhead gas phase 23 to avoid safety problems associated with the presence of excess oxygen in said gas phase. The additional cost of such nitrogen or other gas could well render this embodiment uneconomical from a practical operating viewpoint. In order to render the process of the illustrated embodiment economically feasible, the impeller used therein must be efficient in oxygen transfer by being capable of distributing the oxygen feed as very small bubbles and promoting a longer mean residence time for the oxygen bubbles in the liquid phase.

It will be appreciated that various changes and modifications can be made in the details of the invention as described herein without departing from the scope of the appended claims. The process and system of the invention are suitable for the exothermic oxidation of any organic chemical. For the reasons indicated above, the invention is especially well suited to the oxidation of those organic chemicals whose oxidation produces a solid as the desired product or as a byproduct. Any of the polyalkyl aromatics, such as p-xylene, are examples of organic chemicals for which oxidation using the evaporative cooling approach of the invention is particularly advantageous. In addition to the production of terephthalic acid, the production of any other di-carboxylic acid, such as isophthalic acid, trimellitic acid, and 2,6 naphthaline dicarboxylic acid, are illustrative examples of commercial significant applications of the invention.

As will be seen from the illustrated embodiments, pure oxygen or an oxygen-rich gas is injected directly into the recirculating portion of the body of liquid at an oxygen injection point or points near the impeller means. For purposes of this invention, a position near the impeller means is one within the turbulent flow field produced by the impeller means, including the impeller suction and discharge flow fields. It should be noted that the roll cells, i.e. roll cells B in FIG. 2, formed in the lower region of the reactor vessel below the hollow draft tube and said impeller means constitute a very significant portion of said turbulent flow field produced by said impeller means.

In an illustrative example of the practice of the invention, terephthalic acid is produced by the oxidation of liquid p-xylene in reactor vessel 1 of the FIG. 2 embodiment of the invention. Acetic acid is employed as a solvent, with 500–3,000 ppm of a cobalt/manganese catalyst and bromine in the form of hydrogen bromide being employed as an initiator at a bromine, relative to the total catalyst loading, of 0.3:1. A reaction temperature of about 200° C. is employed at a pressure of 115–180 psia. Essentially pure oxygen is injected through line 17a into the draft tube at the point of very high shear between impeller means 9 and radial mixer 10. As a result, the oxygen rapidly disperses as very small bubbles. Therefore, the oxygen is rapidly consumed upon transfer into the liquid phase. Evaporation of a fraction of the reaction mixture occurs at the reaction conditions employed to remove the heat of reaction by evaporative cooling. Because of the draft tube position and configuration in accordance with the drawing, the reingestation of upward rising gases into the downward flowing liquid at the top of conically flared upper portion 6a of hollow draft tube 6 is minimized. Thus, the possibility of cavitation is significantly reduced or avoided. Likewise, undesired dilution of oxygen reactant in the lower portion of draft tube 6 is avoided. As a result, the oxygen employed is effectively utilized, evaporative cooling is successfully employed and the loss of solvent is very significantly reduced as compared with prior art air based processing for terephthalic acid production.

While essentially pure oxygen is desirably employed in preferred embodiments of the invention other nearly pure oxygen gases can also be used in the practice of the invention. Such nearly pure oxygen, for purposes of the invention, is oxygen-rich gas having a significantly higher oxygen content than air, e.g., oxygen-rich air having at least 50%, preferably at least about 90%, oxygen content.

The invention provides a significant advance in the field of organic chemical oxidation. The highly effective LOR system is desirably modified for use without cavitation, enabling the desirable LOR gas\liquid mixing process and system to be employed with evaporative cooling. Not only does the practice of the invention enable the LOR process and system to be extended effectively to oxidation reactions producing solid products or byproducts, the use of pure or nearly pure oxygen in the practice of the invention enables reaction conditions to be employed such as to reduce undesired byproduct formation and to reduce solvent consumption and gas throughput in the reaction system and waste gas generation. The evaporative cooling feature of the invention offers significant and unexpected benefits in the increased reduction of liquid reactant and solvent consumption. All of these benefits enhance the technical and economic feasibility of carrying out organic chemical oxidation reactions in a variety of practical commercial operations.

We claim:

1. An improved process for the oxidation of organic chemicals present in a body of liquid contained within a reactor vessel, without appreciable loss of oxygen to the overhead gas phase, comprising:

(a) maintaining said body of liquid containing an organic chemical to be oxidized present in an organic solvent in a recirculating flow pattern by impeller means positioned therein, said body of liquid having a gas-liquid interface with an overhead gas phase;

(b) injecting pure oxygen or an oxygen-rich gas directly into said recirculating portion of the body of liquid at an oxygen injection point or points near said impeller means such as to be within the turbulent flow field of high shear produced by said impeller means, so as to rapidly disperse oxygen in the liquid as small bubbles with rapid consumption of at least about 90% of the oxygen upon said injection into the liquid, the heat of reaction due to the oxidation of the organic chemical being removed by evaporative cooling upon evaporation of volatile organic material and water present in said body of liquid, with bubbles of said evaporated organic material and water vapor, accompanied by the small remaining undissolved portion of the injected oxygen, rising upward in said body of liquid and through a relatively quiescent, essentially non-turbulent zone in the upper portion of the reactor vessel to the gas-liquid interface and to said overhead gas phase, said reactor vessel containing no direct contact mechanical cooling means; and (c) venting said bubbles of evaporated organic material and water vapor from the overhead gas phase, whereby the oxygen and the organic chemical to be oxidized are mixed under conditions promoting the rapid consumption of oxygen and the evaporation of organic material and water with minimal amounts of oxygen bubbles being passed to the overhead gas phase.

2. The process of claim 1 and including passing an inert gas through the overhead gas phase to inert small quantities of oxygen passing to the overhead gas phase.

3. The process of claim 1 in which the recirculating liquid flow pattern is maintained in the body of liquid by an axial flow, downward pumping impeller means positioned in the lower half of the reactor vessel, the injection point of pure oxygen or an oxygen-rich gas being in said turbulent flow field produced by the impeller means, said impeller means having a upwardly extending drive shaft and baffle means positioned thereon for preventing the ingestion of gas from the overhead gas phase along said drive shaft and into the liquid passing to the impeller means, the liquid passing downward through said downward pumping impeller means being at a high velocity such as to create high turbulent roll cells that trap undissolved oxygen and enhance the dissolution thereof.

4. The process of claim 3 in which said axial flow, downward pumping impeller means is positioned in the lower portion of an essentially centrally positioned hollow draft tube having open ends at the top and bottom thereof so that the recirculating flow of liquid is downward in the hollow draft tube and upward outside thereof, the hollow draft tube having an enlarged, conically flared upper portion extending upward in vertical distance about 0% to about 200% of the length of the bottom portion thereof, said upper portion having an enlarged upper diameter minimizing the downward velocity of liquid across the top of said hollow draft tube.

5. The process of claim 4 in which the oxygen injection point is in the hollow draft tube below said axial flow, downward pumping impeller means.

6. The process of claim 5 in which radial flow impeller means are positioned in said hollow draft tube below said axial flow, downward pumping impeller means, said oxygen injection point being located between the axial flow, downward pumping impeller means and said radial flow impeller means.

7. The process of claim 5 in which radial flow impeller means are positioned in said hollow draft tube below said downward pumping impeller means, said oxygen injection point being below said radial flow impeller means.

8. The process of claim 4 in which the oxygen injection point is below the hollow draft tube.

9. The process of claim 2 in which said body of liquid is maintained at the boiling point of the reaction mixture with little excess gaseous oxygen being present therein.

10. The process of claim 4 in which the enlarged, conically flared upper portion of the hollow draft tube extends upward from about 100% to about 150% of the length of the bottom portion thereof.

* * * * *